(12) United States Patent
Peterson et al.

(10) Patent No.: US 9,863,928 B1
(45) Date of Patent: Jan. 9, 2018

(54) ROAD CONDITION DETECTION SYSTEM

(71) Applicant: United Parcel Service of America, Inc., Atlanta, GA (US)

(72) Inventors: Erik Peterson, Atlanta, GA (US); Nagesh Kadaba, Roswell, GA (US); Christopher T Schenken, Alpharetta, GA (US)

(73) Assignee: UNITED PARCEL SERVICE OF AMERICA, INC., Atlanta, GA (US)

( * ) Notice: Subject to any disclaimer, the term of this patent is extended or adjusted under 35 U.S.C. 154(b) by 0 days.

(21) Appl. No.: 14/221,248

(22) Filed: Mar. 20, 2014

Related U.S. Application Data

(60) Provisional application No. 61/803,777, filed on Mar. 20, 2013.

(51) Int. Cl.
  *H04N 7/18* (2006.01)
  *G01N 33/42* (2006.01)

(52) U.S. Cl.
  CPC .................................. *G01N 33/42* (2013.01)

(58) Field of Classification Search
  CPC ............... B60R 1/00; B60R 2300/105; B60R 2300/802; B60R 11/04; H04N 7/181
  USPC ................................................. 348/143–148
  See application file for complete search history.

(56) References Cited

U.S. PATENT DOCUMENTS

| | | | |
|---|---|---|---|
| 4,700,223 A | 10/1987 | Shoutaro et al. | |
| 4,899,296 A * | 2/1990 | Khattak | G01B 11/16 348/148 |
| 5,543,177 A * | 8/1996 | Morrison | G03G 9/08 101/491 |
| 6,075,466 A | 6/2000 | Cohen et al. | |
| 6,615,648 B1 * | 9/2003 | Ferguson | G01C 7/04 702/127 |
| 6,842,189 B2 | 1/2005 | Park, II | |
| 6,850,841 B1 | 2/2005 | Casino | |
| 6,947,577 B2 * | 9/2005 | Stam | B60Q 1/085 315/82 |
| 7,102,496 B1 * | 9/2006 | Ernst, Jr. | G08G 1/164 180/167 |
| 7,151,996 B2 | 12/2006 | Stein | |
| 7,869,935 B2 * | 1/2011 | Ma | G06K 9/00785 701/117 |

(Continued)

FOREIGN PATENT DOCUMENTS

EP           0215948 A1    4/1987

*Primary Examiner* — Tung Vo
(74) *Attorney, Agent, or Firm* — Alston & Bird LLP

(57) ABSTRACT

The present invention is directed to a road condition detection system for identifying and monitoring road conditions, and for communicating information regarding road conditions to various users. The road condition detection system is provided for capturing data indicative of road conditions and analyzing the captured data to locate and identify various road conditions (e.g., road hazards, such as potholes, or weather conditions, such as ice). In various embodiments, the road condition detection system includes a road condition sensor array configured for being attached to a vehicle and for capturing road condition data. The captured data may be transmitted and assessed by a server configured for identifying potential road hazards or other road conditions based on the road condition data captured by the sensor array.

12 Claims, 3 Drawing Sheets

(56) References Cited

U.S. PATENT DOCUMENTS

Figure 1:
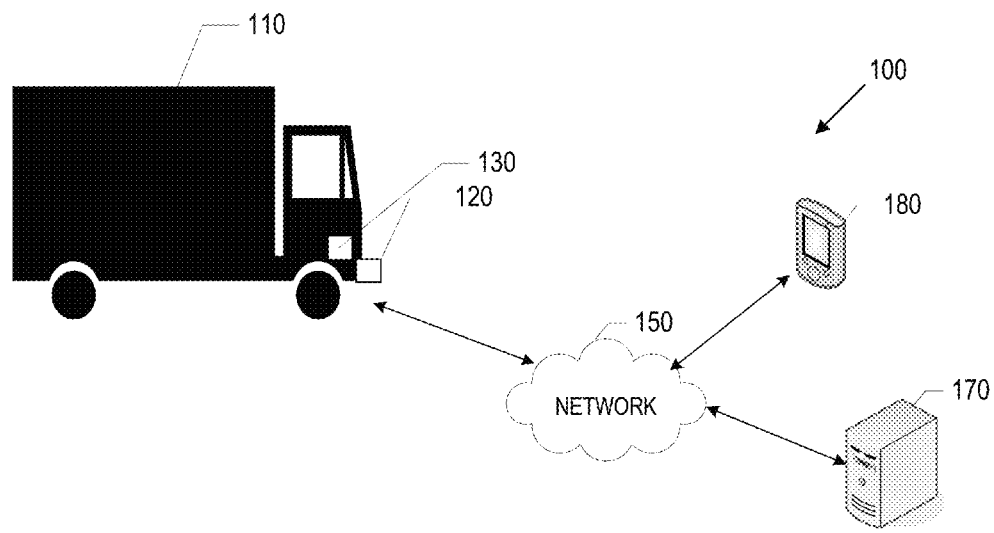

| | | | |
|---|---|---|---|
| 8,005,775 B2 * | 8/2011 | Bridgewater | G06Q 10/06 706/45 |
| 8,655,951 B2 * | 2/2014 | Sloop | G01C 21/3691 340/471 |
| 8,688,332 B2 * | 4/2014 | Reiners | E02F 9/2054 701/33.4 |
| 9,038,473 B2 * | 5/2015 | Gruca, Jr. | G01N 29/048 73/633 |
| 2006/0062965 A1 * | 3/2006 | Durant | G02B 5/128 428/143 |
| 2006/0276985 A1 * | 12/2006 | Xu | G01C 11/025 702/81 |
| 2007/0098245 A1 * | 5/2007 | Mylaraswamy | G01N 21/8851 382/141 |
| 2008/0103835 A1 * | 5/2008 | Corcoran | G06Q 10/0637 705/4 |
| 2010/0112340 A1 * | 5/2010 | Bell | B05D 5/063 428/332 |
| 2012/0029809 A1 | 2/2012 | Lee et al. | |
| 2012/0033851 A1 * | 2/2012 | Chen et al. | G06T 7/0002 382/100 |
| 2013/0027511 A1 * | 1/2013 | Takemura | G06K 9/00805 348/42 |
| 2013/0030680 A1 * | 1/2013 | Friedlander | B60W 40/06 701/117 |
| 2013/0151058 A1 * | 6/2013 | Zagorski | B60W 30/09 701/23 |
| 2013/0194565 A1 * | 8/2013 | Sorensen | G01N 21/55 356/73 |
| 2014/0062725 A1 * | 3/2014 | Maston | G08G 1/0112 340/905 |
| 2014/0067265 A1 * | 3/2014 | Maston | G01C 21/3697 701/533 |
| 2014/0160295 A1 * | 6/2014 | Kyomitsu | G08G 1/0112 348/159 |
| 2015/0371094 A1 * | 12/2015 | Gardiner | E01C 23/01 348/148 |

\* cited by examiner

ROAD CONDITION DETECTION SYSTEM

CROSS-REFERENCE TO RELATED APPLICATIONS

This application claims the benefit of U.S. Provisional Application No. 61/803,777, filed Mar. 20, 2013, the entirety of which is hereby incorporated by reference.

BACKGROUND OF THE INVENTION

Field of the Invention

Various embodiments of the present invention described herein generally relate to a road condition detection system for detecting and monitoring road conditions.

Description of Related Art

Various road conditions may make a road difficult to navigate or increase the risk of damage to a vehicle driving on the road. Some of these conditions include road imperfections (e.g., potholes, bumps, and cracks), weather conditions (e.g., wet or icy roads), low visibility (e.g., due to street lights being out), or debris in the road (e.g., tree limbs, gravel, and car accident debris). If one of these conditions is present on a given road, it would be advantageous for drivers to be notified so they may avoid a particular road hazard or hazardous road condition. Additionally, it would be advantageous for appropriate agencies, such as the local Department of Transportation, to be notified so that hazardous conditions can be addressed and the public may be apprised of current road conditions.

Several media outlets exist that inform drivers of road conditions, such as local news stations, local radio stations, and online traffic sites. Similarly, government agencies (e.g., Department of Transportation) have systems that enable drivers to report roadway conditions to the appropriate personnel. However, the above-described media outlets and agencies often depend on people manually reporting road conditions. For example, if a driver sees a hazardous condition on a given road, the driver may call the Department of Transportation and describe the condition and its location (e.g., a pothole or patch of ice). In order to address the road condition, the Department of Transportation may first send a crew to locate the condition, which may be difficult to do depending on the description given by the driver. Furthermore, information regarding the road condition may become inaccurate through the chain of communication (e.g., where one DOT employee describes the condition inaccurately to another responsible for a repair or inspection). In addition, the crew may also need to inspect the identified road condition to determine what must be done to address it. At some later point in time, a separate crew may be sent to address the condition. This process is often imprecise and inefficient, thereby resulting in lingering hazardous road conditions posing a continuing threat to drivers and vehicles.

Accordingly, there is an ongoing need in the art for systems and methods for more efficiently identifying and reporting road conditions.

BRIEF SUMMARY OF THE INVENTION

Various embodiments of the present invention are directed to a system for detecting and monitoring road conditions. According to various embodiments, the system comprises one or more memory storage areas and one or more processors in communication with the one or more memory storage areas. The processors are, collectively, configured to: receive road condition data captured by one or more road condition detection systems provided on one or more vehicles, wherein the road condition data is indicative of one or more road condition attributes of one or more road surfaces traveled by the one or more vehicles; identify, based on the received road condition data, one or more road hazards existing on the one or more road surfaces, the one or more road hazards each comprising an identified road condition that is at least potentially hazardous to a vehicle traversing the road surface; determine, based on the received road condition data, the location of the identified one or more road hazards; and store data indicative of the identified one or more road hazards and their respective locations in the one or more memory storage areas.

Various embodiments of the present invention also include a system for detecting road conditions including at least one road condition sensor array configured for being mounted to a vehicle, the road condition sensor array comprising one or more sensing devices configured capturing road condition data indicative of one or more road condition attributes of one or more road surfaces traveled by the vehicle; at least one processor configured for controlling the operation of the at least one road condition sensor array; and one or more memory storage areas configured for storing the road condition data captured by the road condition sensor array.

BRIEF DESCRIPTION OF THE SEVERAL VIEWS OF THE DRAWING(S)

Figure 2:
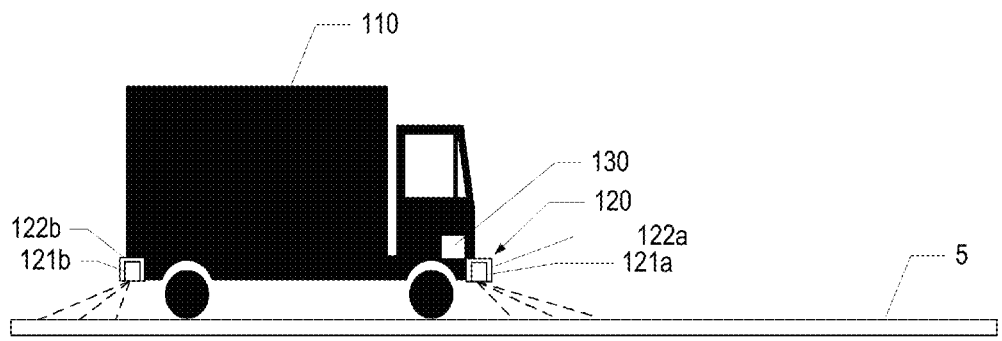
Figure 3:
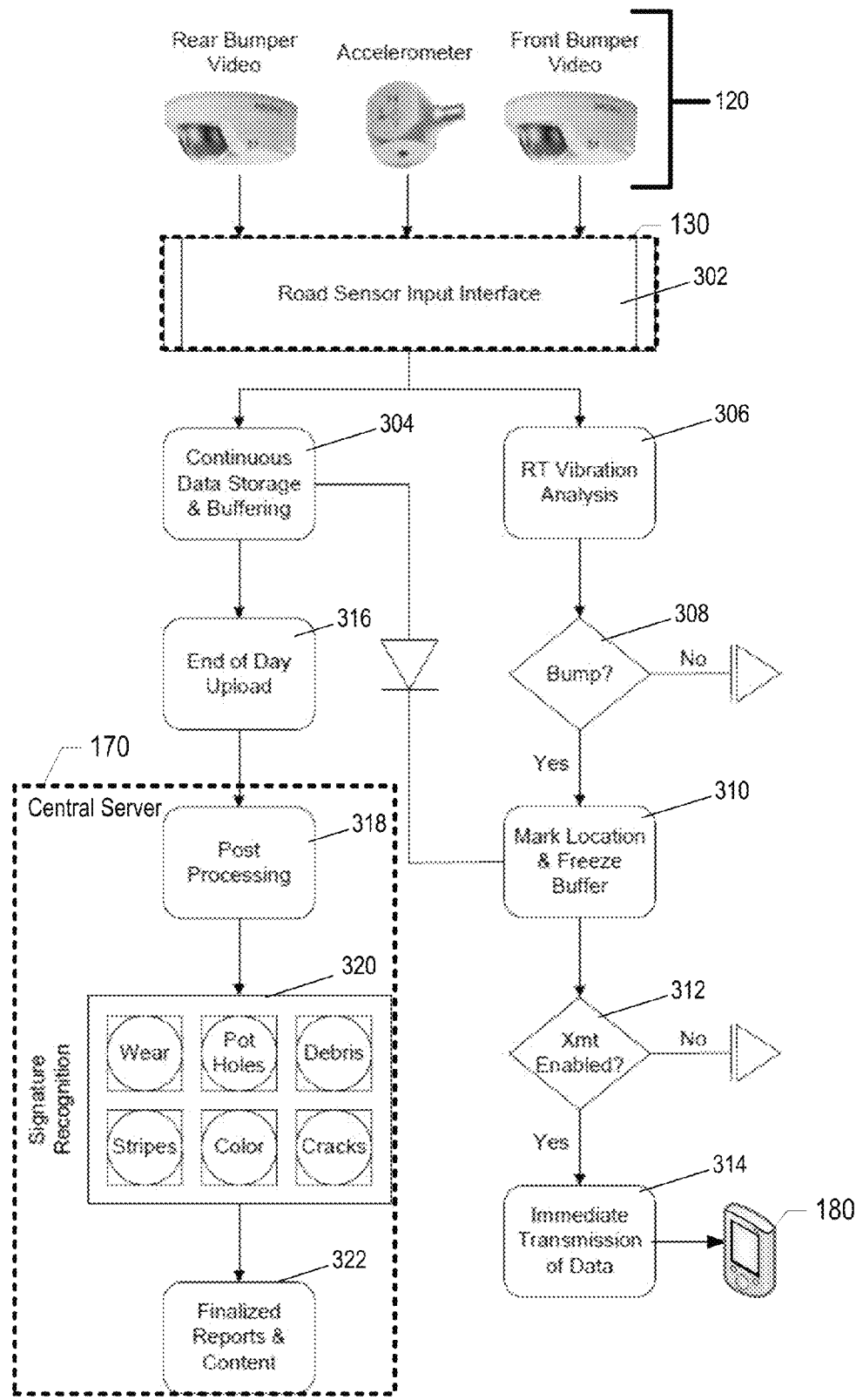
Figure 4:
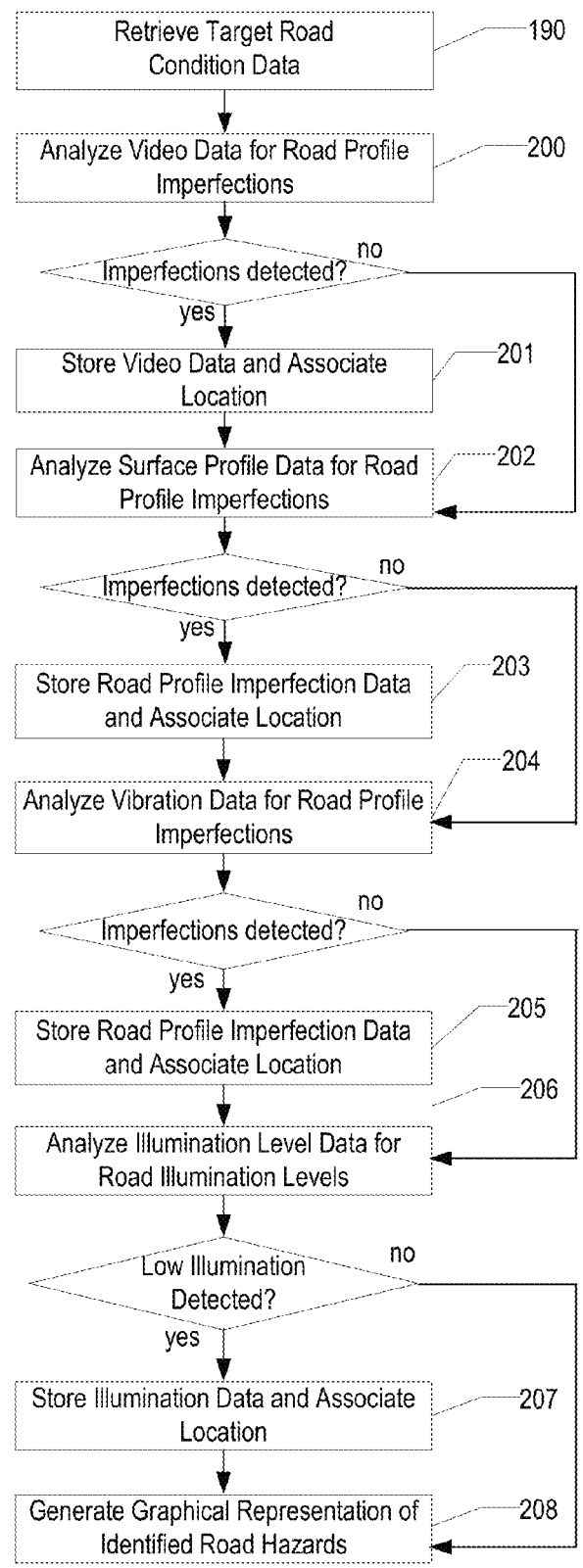

Reference will now be made to the accompanying drawings, which are not necessarily drawn to scale, and wherein:

FIG. 1 is a schematic block diagram of a road condition detection system according to one embodiment of the present invention;

FIG. 2 is a schematic block diagram of road condition sensor array adapted for use on a vehicle according to one embodiment of the present invention; and FIG. 3 is a flow diagram of steps executed by a road condition detection system according to one embodiment of the present invention; and FIG. 4 is a flow diagram of steps executed by a central server according to another embodiment of the present invention.

DETAILED DESCRIPTION OF THE INVENTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Overview

The present invention relates to systems and methods for identifying and monitoring road conditions, and for communicating information regarding road conditions to various users. According to various embodiments, a road condition detection system is provided for capturing data indicative of road conditions and analyzing the captured data to locate and identify various road conditions (e.g., road hazards, such as potholes, or weather conditions, such as ice). In various embodiments, the road condition detection system comprises a road condition sensor array configured for being attached to a vehicle and for capturing road condition data, an onboard computer for analyzing the road condition data in real time and transmitting information regarding road conditions to remotes users of the system, and a central data analysis server configured for conducting post processing analysis of the data collected by the road condition sensor array to determine additional information about various road conditions.

In various embodiments, the road condition sensor array is configured to sense and record information about a given road as the vehicle travels along the road. For example, the road condition sensor array may include an optical camera, a vibration sensor, a road surface scanner, and various other devices configured to capture road condition data indicative of various road condition attributes, such as a road's surface profile, imperfections, illumination level, reflectivity, and/or other conditions. The road condition sensor array may also include, or may be in communication with, a geo-location device, allowing the system to geo-code the location of road condition data indicative of these attributes. According to various embodiments, a plurality of vehicles in a fleet (e.g., a fleet of delivery vehicles) may each be equipped with a road condition sensor array, thereby capturing road condition data for various roads over a wide area at various times.

In various embodiments, the road condition data collected by the road condition sensor array may be processed and stored (in whole or in part) by an onboard vehicle computer. In addition, the data capturing operations of the road condition sensor array may be controlled by the onboard computer, which may dictate when the road condition sensor array captures road condition data and the frequency with which it does so. In addition, the onboard computer may include various telematics devices and sensors monitoring dynamic attributes of the vehicle, or may be in communication with a separate telematics devices or sensors provided on the vehicle.

As described in greater detail below, the road condition data captured by the road condition sensor array may be analyzed by the onboard computer in order to identify various road conditions based on the road condition data (e.g., bumps, potholes, debris, wet or icy conditions, etc). Information advising users of these various conditions may then be transmitted from the onboard computer to one or more users devices in real time over a network. In addition, the road condition data may be analyzed further by the central server to identify additional road conditions (e.g., more detailed information regarding cracks and potholes, visibility conditions, weather conditions, etc.). In addition, the central data analysis server may be configured to create data applied to maps indicating various road conditions (e.g., layers applied to digital maps), calculate a road condition index for individual roads or areas, and compare changes in road conditions for particular roads or locations. The analyses performed by the central server may be useful, for example, in identifying and communicating road conditions to drivers and for evaluation of road repairs and maintenance.

Road Condition Detection System

FIG. 1 shows a road condition detection system 100, according to one embodiment. In the illustrated embodiment, the road condition detection system 100 generally comprises a road condition sensor array 120 mounted on a vehicle 110, an onboard computer 130, and a central data analysis server (herein "central server") 170. As discussed in greater detail below, the onboard computer 130 is configured to communicate with the road condition sensor array 120 in order to control the capture and storage of road condition data. The onboard computer 130 is further configured to communicate with the central server 170 via a communication network 150 in order to transmit road condition data to the server 170 for analysis. Additionally, the central server 170 and onboard computer 130 may be configured to communicate with one or more user devices 180 (e.g., a mobile phone, tablet computer, digital information acquisition device, or the like) to provide updated road condition data to a user. The components of the illustrated embodiment are discussed in more detail below.

Road Condition Sensor Array

FIG. 2 shows a road condition sensor array 120 mounted on a vehicle 110 according to one embodiment. In the illustrated embodiment, the road condition sensor array 120 generally comprises a front sensing unit 121a housed within a detachable front mounting housing 122a, and a rear sensing unit 121b housed within a detachable rear mounting housing 122b. According to various embodiments, the front sensing unit 121a comprises various road image detection devices, including an optical camera, a vibration sensor, and a road surface scanner. As the vehicle 110 drives along a road 5, the road condition sensor array's sensing unit 121a captures road condition data relating to the conditions of the road 5. For example, the captured road condition data may include video data, surface profile data, illumination level data, vibration data, and other data generated by other devices in the sensing unit 121a. As described in greater detail below, the sensing unit's devices are in communication with the vehicle's onboard computer 130, which may be configured to control the operation of the sensing unit 121a and store captured road condition data.

In various embodiments, the sensing unit 121a includes an optical camera configured to capture video and/or still images of the road surface and detect the illumination level of the road 5. For example, in one embodiment, the optical camera may be configured to capture video of the road surface continuously as the vehicle 110 travels. In such embodiments, the onboard computer 130 may continuously store video data generated by the optical camera and may be configured to buffer and transmit data to a user device 180.

According to various embodiments, the optical camera may also be configured to receive light from the road through an aperture in the camera housing, which may vary in size to control the amount of light reaching the optical sensor. The optical sensor is configured to detect the intensity of the light received through the aperture resulting in illumination level data corresponding to the illumination level of the road 5 at a given point. Accordingly, if the vehicle 110 is traveling at night along a lighted road and passes by an area where street lights are out, the illumination level data will indicate a reduction in luminous intensity. Similarly, the illumination level data may indicate poor illumination in tunnels, under bridges, or in covered areas (e.g., parking lots). In this way the optical camera is able to capture illumination level data indicative of a particular road's varying illumination levels along the distance traveled by the vehicle 110.

In various embodiments, the optical camera may be further configured to detect the reflectivity of the surface of the road 5. This may be accomplished, for example, by the camera emitting light (e.g., via a flash bulb or LED bulb) and detecting the level of light reflected by the road surface. As such, the optical camera is able to capture reflectivity data indicative of the surface reflectivity of the road 5 at any given point. Accordingly, if a road surface is wet (e.g., due to rain or an oil leak) or coated with another hazardous substance, the reflectivity data will indicate a comparative increase in the reflectivity of the road surface. Likewise, where the road is dry, the reflectivity data will indicate a comparative decrease in the reflectivity of the road surface. In this way, the optical camera is also able to capture reflectivity data indicative of a particular road's varying reflectivity along the distance traveled by the vehicle 110.

As will be appreciated from the description herein, the optical camera may be configured to capture video data, illumination level data, and reflectivity data, or two or more cameras may be provided, each being configured to capture illumination level data or reflectivity data. In addition, a lens may be disposed within the camera housing aperture and a shutter and/or lens cover may cover the lens when the camera is not actively recording illumination level data or reflectivity data. In this way, the shutter and/or lens cover may protect the lens from damage such as being scratched or cracked. In other embodiments, the illumination level data and reflectivity data may be captured via other suitable devices, such as laser sensors or the like.

In addition to the optical camera, the sensing unit 121a may include a road surface scanner may comprise a laser or electromagnetic sensor disposed within a scanner housing. As the vehicle travels along the road 5, the sensor is configured to scan the surface of the road 5 and capture surface profile data indicative of the road's surface profile. Accordingly, if the vehicle 110 travels over a pothole, the captured surface profile data will indicate a depression in the road surface. Likewise, if the vehicle 110 travels over piece of debris or other object on the surface of the road 5, the captured surface profile data will indicate a protrusion on the road surface. In this way, the road surface scanner is able to capture surface profile data indicative of a particular road's full surface profile along the distance traveled by the vehicle 110.

As noted above, the sensing unit 121a also includes a vibration sensor configured to capture vibration data indicative of the magnitude and frequency of vibration of the vehicle 110 as it travels along the road. For example, in one embodiment, the vibration sensor is configured to detect vibrations in the vehicle's chassis (e.g., vibrations transmitted from the road surface through the wheels and suspension to the chassis). Accordingly, if the vehicle 110 travels over a pot hole, the vibration data captured by the vibration sensor will indicate a sharp change in vibration magnitude or frequency. Additionally, if the vehicle 110 is traveling a smooth road, the vibration data will indicate a low-magnitude, consistent vehicle vibration, while a rough road will result in inconsistent vibration data corresponding to various bumps and imperfections in the road surface. In this way, the vibration sensor is also able to capture vibration data indicative of the smoothness of a particular road along the distance traveled by the vehicle 110.

According to various embodiments, the sensing unit 121a may further comprise an infrared camera, a noise detecting device, and/or other road condition detecting devices. For example, the infrared camera may be used for capturing infrared data indicative of hot spots on the road surface while the noise detecting device may be used for capturing noise data indicative of loud noises associated with a vehicle traveling over a pot hole or other debris. Indeed, as will be appreciated from the description herein, the sensing unit 121a may include any road condition detecting device capable of detecting useful data indicative of one or more road conditions. Additionally, in some embodiments, the various cameras and/or sensors of the road condition sensor array 120 may have zoom capabilities in order to capture road condition data with at varying degrees of granularity.

As shown in FIG. 2, the various devices of the sensing unit 121a are secured within a mounting housing 122a. In the illustrated embodiment, the mounting housing 122a is mounted to the front bumper of vehicle 110 and faces the road surface directly in front of the vehicle 110 (e.g., as indicated by the dashed lines in FIG. 2). In certain embodiments, the mounting housing 122 includes a quick release mechanism configured to engage a mating member on the vehicle's front bumper. This allows the sensing unit 121a to be easily removed from vehicle 110 and easily mounted on another vehicle. Moreover, as will be appreciated from the description herein, the vehicle 110 may include a plurality of mating members positioned at various locations on the vehicle 110 (e.g., front bumper, rear bumper, centrally underneath vehicle, side of vehicle frame, etc.) such that the one or more road condition sensor arrays 120 can be secured at various locations on the vehicle 110.

In the illustrated embodiment, the road condition sensing array 120 also includes a rear sensing unit 121b secured within a rear mounting housing 122b. According to various embodiments, the rear sensing unit 121b may comprise the same, or one or more of, the various sensors and detection devices provided in the front sensing unit 121a. In addition, the rear mounting housing 122b may be substantially the same as, or similar to, the front mounting housing 122a. As will be appreciated from FIG. 2, the provision of both front and rear sensing units 121a, 122b enables the road condition sensing array 120 to capture additional road condition data to verify various road conditions. Indeed, in certain embodiments, the rear sensing unit 121b may be configured to capture road condition data to confirm road conditions indicated by the road condition data captured by the front sensing unit 121a.

In various other embodiments, the sensing units 121a, 121b and mounting housings 122a, 122b may be provided at any suitable location on the vehicle 110 depending on its configuration and intended use. In addition, according to various embodiments, less or additional sensing units may be provided as needed. For example, in certain embodiments only a single front or rear sensing unit may be provided. In other embodiments, additional sensing units may be placed on lateral sides of the vehicle.

Onboard Computer & Communications Network

According to various embodiments, the road condition sensor array's sensing units 121a, 121b may be controlled by the vehicle's onboard computer 130. In various embodiments, the onboard computer 130 comprises at least one processor, a location-determining device or sensor (e.g., a GPS sensor), a real-time clock, J-Bus protocol architecture, an electronic control module (ECM), a port for receiving data from vehicle sensors located on the vehicle 110, a communication port for receiving instruction data, a radio frequency identification (RFID) tag, a power source, a data radio for communication with a WWAN, a WLAN and/or a WPAN, a programmable logic controller (PLC), and one or more memory storage devices. The memory storage devices may include volatile memory and/or non-volatile memory, which can be embedded and/or may be removable. For example, the non-volatile memory may be embedded or removable multimedia memory cards ("MMCs"), secure digital ("SD") memory cards, Memory Sticks, EEPROM, flash memory, hard disk, or the like. The memory storage device may also include DRAM and NVRAM memory modules. In other embodiments, various components of the onboard computer 130 (e.g., the RFID tag, the location sensor, and the PLC) may be located in the vehicle 110, external from the onboard computer 130.

The onboard computer's location sensor may be, for example, a GPS-based sensor compatible with a low Earth orbit (LEO) satellite system, medium Earth orbit satellite system, or a Department of Defense (DOD) satellite system. Alternatively, triangulation may be used in connection with various cellular towers positioned at various locations throughout a geographic area in order to determine the location of the vehicle 110. The location sensor may be used to receive position, time, and speed data. In addition, the location sensor may be configured to detect when its vehicle 110 has entered or exited a GPS-defined geographic area (e.g., a geo-fenced area). As will be appreciated from the description herein, more than one location sensor may be utilized, and other similar techniques may likewise be used to collect geo-location information associated with the vehicle 110.

In addition, various embodiments of the onboard computer 130 may include multiple processors configured for carrying out the various processes described herein. As will be appreciated from the description herein, the onboard computer 130 may not include certain of the components described above, and may include any other suitable components in addition to, or in place of, those described above. As an example, the onboard computer 130 may include various types of communications components (e.g., to support new or improved communications techniques).

In the illustrated embodiment, the onboard computer 130 is generally configured to communicate with the road condition sensor array's sensing units 121a, 121b in order to (i) control when the sensing units 121a, 122b capture road condition data, (ii) store the road condition data captured by the sensing units 121a, 122b, and (iii) transmit the stored road condition data to the central server 170 and/or the user device 180. For example, in one embodiment, the onboard computer 130 causes the sensing units 121a, 122b to capture road condition data continuously as the vehicle 110 travels. In other embodiments, the onboard computer 130 causes the sensing units 121a, 122b to capture road condition data at given time intervals when the vehicle 110 is on (e.g., such that all of the sensing unit's sensors capture data every second, every 2 seconds, or every 5 seconds). In other embodiments, the onboard computer 130 causes the sensing units 121a, 122b to capture road condition data at given distance intervals as the vehicle 110 travels down road 5 (e.g., such that all of the sensing unit's sensors capture data every 5 feet, every 10 feet, or every 50 feet traveled).

In further embodiments, the onboard computer 130 causes the sensing units 121a, 122b to start or stop capturing road condition data when the vehicle 110 changes direction, goes over a bump, or accelerates. In addition, the onboard computer 130 may be configured to monitor signals received from the sensing units 121a, 122b and capture data only when certain predefined parameters are met (e.g., illumination intensity below a predefined valued or a road surface profile deviating more than a certain amount from a predefined base profile). Moreover, the onboard computer 130 may be configured to trigger data capture by one or more specific devices in the sensing units 121a, 122b according to the criteria above. Indeed, as will be appreciated from the description herein, the onboard computer 130 may be programmed to trigger data capture by the sensing units 121a, 122b according to any desirable parameters.

As noted above, the onboard computer 130 includes a location-determining device or sensor, such as a GPS sensor, and a real-time clock. Accordingly, in various embodiments, the onboard computer 130 may be configured to associate and store location and/or date and time information—e.g., as indicated by the location sensor and clock—with the road condition data collected by the road condition sensor array 120. By associating location and date and time information with the road condition data captured by the road condition sensor array 120, the physical and temporal location of a road hazard indicated by the road condition data may be determined (e.g., by the central server 170 as explained below).

In various embodiments, the road condition data captured by the road condition sensor array 120 may be stored in the onboard computer 130 (e.g., in the computer's memory storage devices). For example, in certain embodiments, the onboard computer 130 is configured to store road condition data collected by the road condition sensor array 120 continuously as it is captured. In other embodiments, the onboard computer 130 is configured to store road condition data collected by the road condition sensor array 120 only if the onboard computer 130 detects a deviation in the road condition data that may indicate the presence of a road hazard (e.g., a change in vibration frequency or road surface profile). In yet another embodiment, the onboard computer 130 is configured to store only road condition data captured within a particular geo-fenced area.

As described in greater detail below, the road condition data captured by the road condition sensor array 120 and stored by the onboard computer 130 is transmitted to the central server 170 via a communications network 150. According to various embodiments of the present invention, the communications network 150 may be capable of supporting communication in accordance with any one or more of a number of second-generation (2G), 2.5G and/or third-generation (3G) mobile communication protocols or the like. More particularly, the network 150 may be capable of supporting communication in accordance with 2G wireless communication protocols IS-136 (TDMA), GSM, and IS-95 (CDMA). Also, for example, the network 150 may be capable of supporting communication in accordance with 2.5G wireless communication protocols GPRS, Enhanced Data GSM Environment (EDGE), or the like. In addition, for example, the network 150 can be capable of supporting communication in accordance with 3G wireless communication protocols such as Universal Mobile Telephone System (UMTS) network employing Wideband Code Division Multiple Access (WCDMA) radio access technology. Some narrow-band AMPS (NAMPS), as well as TACS, network(s) may also benefit from embodiments of the present invention, as should dual or higher mode mobile stations (e.g., digital/analog or TDMA/CDMA/analog phones). As yet another example, the network 150 may support communication in accordance with techniques such as, for example, radio frequency (RF), Bluetooth™, infrared (IrDA), or any of a number of different wireless networking techniques, including Wireless LAN (WLAN) techniques.

In certain embodiments, the onboard computer 130 may be configured to transmit stored road condition data whenever it is able to establish a successful connection with the central server 170 via a WLAN component of the network 150 (e.g., when the vehicle 110 returns to a hub broadcasting a wireless networking signal). In addition, the onboard computer 130 may be further configured to immediately transmit (e.g., via 3G cellular network) captured road condition data meeting predefined "alert" parameters (e.g., road condition data clearly indicating a road hazard, such as a pothole or debris). In such embodiments, the onboard computer 130 (and/or central server 170) may be further configured to transmit the alert-status road condition data to the Department of Transportation, local media outlets, or other online road condition services in order to provide real-time status updates for various roads.

Central Server

According to various embodiments, the road condition data captured by the road condition sensor array 120 and stored by the onboard computer 130 may be subsequently transmitted over the network 150 to the central server 170 for post processing. As will be appreciated from the description herein, the central server 170 includes various devices for performing one or more functions in accordance with embodiments of the present invention, including those more particularly shown and described herein. However, various embodiments of the central server 170 may include alternative devices for performing one or more like functions without departing from the spirit and scope of the present invention.

In various embodiments, the central server 170 includes a processor that communicates with other elements within the central server 170 via a system interface or bus. In some embodiments, the central server 170 includes a display device/input device for receiving and displaying data. This display device/input device may be, for example, a keyboard or pointing device that is used in combination with a monitor. In certain embodiments, the central server 170 may not include a display device/input device and may be alternatively accessed by a separate computing device (e.g., a networked workstation) having a display device and input device. The central server 170 further includes memory, which preferably includes both read only memory (ROM) and random access memory (RAM). The server's ROM is used to store a basic input/output system (BIOS), containing the basic routines that help to transfer information between elements within the central server 170.

In addition, the central server 170 includes at least one storage device—such as a hard disk drive, a floppy disk drive, a CD Rom drive, or optical disk drive—for storing information on various computer-readable media, such as a hard disk, a removable magnetic disk, or a CD-ROM disk. As will be appreciated by one of ordinary skill in the art, each of these storage devices is connected to the system bus by an appropriate interface. The storage devices and their associated computer-readable media provide nonvolatile storage for a personal computer. It is important to note that the computer-readable media described above could be replaced by any other type of computer-readable media known in the art.

A number of program modules may be stored by the various storage devices and within RAM. Such program modules include an operating system and/or a plurality of program modules (e.g., one or more modules configured for analyzing road condition data). According to various embodiments, the modules control certain aspects of the operation of the central server 170 with the assistance of the processor and operating system.

Also located within the central server 170 is a network interface for interfacing and communicating with other elements of a computer network. It will be appreciated by one of ordinary skill in the art that one or more of the central server 170 components may be located geographically remotely from other central server 170 components. Furthermore, one or more of the components may be combined, and additional components performing functions described herein may be included in the central server 170.

While the foregoing describes a single processor, as one of ordinary skill in the art will recognize, the central server 170 may comprise multiple processors operating in conjunction with one another to perform the functionality described herein. In addition to the memory, the processor can also be connected to at least one interface or other means for displaying, transmitting and/or receiving data, content or the like. In this regard, the interface(s) can include at least one communication interface or other means for transmitting and/or receiving data, content or the like, as well as at least one user interface that can include a display and/or a user input interface. The user input interface, in turn, can comprise any of a number of devices allowing the entity to receive data from a user, such as a keypad, a touch display, a mouse, a joystick or other input device.

While reference is made to a central "server" 170, as one of ordinary skill in the art will recognize, embodiments of the present invention are not limited to a client-server architecture. The system of embodiments of the present invention is further not limited to a single server, or similar network entity or mainframe computer system. Other similar architectures including one or more network entities operating in conjunction with one another to provide the functionality described herein may likewise be used without departing from the spirit and scope of embodiments of the present invention. For example, a mesh network of two or more personal computers (PCs), or similar electronic devices, collaborating with one another to provide the functionality described herein in association with the central server 170 may likewise be used without departing from the spirit and scope of the present invention.

In the illustrated embodiment, the central server 170 is configured to receive road condition data from the onboard computer 130 via network 150. For example, in certain embodiments, the central server 170 may receive a substantially real-time data feed via network 150. In other embodiments, the central server 170 may receive road condition data downloaded from the onboard computer 130 when the vehicle 110 is in range of a WLAN.

Processing of Road Condition Data

FIG. 3 illustrates steps executed by the road condition detection system 100 to analyze captured road condition data according to one embodiment. As shown in FIG. 3, the process begins at step 302 where road condition data captured by the road condition sensor array 120 is transmitted to the onboard computer 130 via a road sensor input interface. Next, at step 204, the onboard computer 130 performs continuous storage and buffering of the road condition data received from the sensor array 120.

Simultaneously, in step 306, the onboard computer 130 analyzes the vibration data present in the road condition data. At step 308, the onboard computer determines whether a bump has been indicated by the vibration data. For example, where the vehicle travels over a pothole or piece of debris, the vibration data captured by the sensor array's vibration sensor (e.g., an accelerometer) will indicate a sharp change in vibration. If a bump is detected, the onboard computer moves to step 310 where it marks the road condition data corresponding to the detected bump and freezes the data buffer (e.g., saving and marking the previous one minute of data).

Next, at step 312, the onboard computer 130 determines whether real time transmission of road condition information is enabled. If real time transmission is enabled, the onboard computer 130 moves to step 314 where it immediately transmits road condition data captured around the impact of the detected bump. For example, in one embodiment, the onboard computer 130 may immediately transfer the relevant road condition data to the central server 170 for processing and transmission to various user devices 180. In other embodiments, the onboard computer 130 may be configured to be configured to immediately transmit the relevant road condition data directly to a user device 180. In yet another embodiment, the onboard computer 130 may be configured to immediately generate and transmit road condition information indicative of the detected bump and/or any related road conditions to the user device 180. In this way, hazardous conditions may be transmitted in real-time wirelessly to users for immediate updates regarding road conditions.

Turning now to step 316, the onboard computer 130 is further configured to perform an end-of-day upload of all captured road condition data. For example, as noted above, in one embodiment the onboard computer 130 may be configured to transmit all captured road condition data to the central server 170 at the end of work day when a WLAN connection can be established with the central server. Next, at step 318, post processing of the captured road condition data is performed by the central server 170. In certain embodiments, this may include reformatting the data and associating the captured road condition data with GPS coordinates and time stamp data to provide context to the captured road condition data.

Next, at step 320, the central server next performs signature recognition analyses of the road condition data to determine further information regarding road conditions. These analyses are described in greater detail below in regard to the exemplary method shown in FIG. 4. Finally, at step 322, the central server 170 generates finalized reports and contents for distribution to various user devices 180. The reports and content may include, but are not limited to, map data for display on existing digital maps indicating one or more road conditions (e.g., on Google Maps), reports on the conditions of roads in certain areas, text messages alerting users to various road hazards, and the like. In certain embodiments, a report may be generated where a user may use a viewer to fast forward through video data to locations where hazardous road conditions have been identified.

Referring back to step 320 in greater detail, various embodiments of the central server 170 are generally configured for analyzing road condition data received from the onboard computer 130 to identify hazardous road conditions indicated by signatures in the data. In various embodiments, the central server 170 includes a pattern recognition module for processing the road condition data. As described in greater detail below, the pattern recognition module is generally configured for sensing deviations in the road condition data which may indicate various specific road conditions or road hazards.

FIG. 4 illustrates steps executed by the pattern recognition module according to one embodiment. Beginning at step 190, the pattern recognition module identifies and retrieves target road condition data. For example, in certain embodiments, a user may request that the central server 170 analyze data for a particular area (e.g., a geo-fenced area such as a county, city, highway, neighborhood, or the like) received during a particular time period (e.g., within the past week). In this case, the pattern recognition module would review the road condition data it has received from the onboard computer 130 and identify road condition data captured at locations within the user-specified area during the user-specified time period. As will be appreciated from the description herein, the pattern recognition module may be configured to retrieve target data relating to any set of user parameters.

Next, at step 200, the pattern recognition module analyzes the video data (e.g., the video or image data captured by the sensing unit's optical camera) present in the retrieved road condition data to identify potential road imperfections. For example, as the vehicle 110 travels along the road 5 in FIG. 2, the video data will show relatively consistent images of the road surface. However, where potholes, cracks, debris, or other imperfections are present, the pattern recognition module will identify these deviations in the image signature and associate them with road imperfections. If the pattern recognition module detect imperfections in the road's surface based on the video data, the module moves to step 201 where the associated data is stored (e.g., in the server's memory storage areas). In addition, at step 201, the pattern recognition module will determine the location and time of the captured data associated with the road imperfection and associate this location/time data with the stored video data for use in generating images of road imperfections.

Next, at step 202, the pattern recognition module analyzes the surface profile data (e.g., data captured by the sensing unit's road surface scanner) present in the retrieved target road condition data to identify potential road imperfections. For example, as the vehicle 110 travels along the road 5 in FIG. 2, the surface profile data will indicate a relatively consistent road profile (e.g., a consistent detected distance from the scanner to the road surface). However, where the vehicle 110 travels over a pothole or piece of debris in the road, the surface profile data will deviate significantly and indicate an abnormal surface profile. Accordingly, the pattern recognition module is configured to identify deviations or abnormalities in the surface profile data. In addition, the pattern recognition module may be configured to compare the surface profile data in the target data with historical surface profile data to identify changes in the road surface profile over a period of time (e.g., by comparing earlier surface profile measurements captured at a particular location with the most recent surface profile measurement for the particular location to identify surface profile deviations or abnormalities).

As shown in FIG. 4, if the pattern recognition module does not detect imperfections in the road's surface profile based on the surface profile data, the module moves to step 204. However, if the pattern recognition module does detect imperfections in the road's surface profile, the module moves to step 203 where the associated data is stored (e.g., in the server's memory storage areas). In addition, at step 203, the pattern recognition module will determine the location and time of the captured data associated with the road imperfection and associate this location/time data with the stored surface profile data for use in generating graphical representations of road imperfections.

Next, at step 204, the pattern recognition module analyzes the vibration data (e.g., data captured by the sensing unit's vibration sensor) present in the retrieved target road condition data to identify potential road imperfections. For example, as a vehicle 110 travels along the road 5 in FIG. 2, the vibration data will indicate relatively consistent road profile (e.g., a consistent vibration frequency detected as the vehicle 110 moves). However, where the vehicle 110 travels over a pothole or piece of debris in the road, the vibration data will deviate significantly and indicate an abnormal surface profile (e.g., a sharp change in vibration frequency or magnitude). Accordingly, the pattern recognition module is configured to identify deviations or abnormalities in the vibration data.

As shown in FIG. 4, if the pattern recognition module does not detect imperfections in the road's surface profile based on the vibration data, the module moves to step 206. However, if the pattern recognition module does detect imperfections in the road's surface profile, the module moves to step 205 where the associated data is stored (e.g., in the server's memory storage areas). In addition, at step 205, the pattern recognition module will again determine the location and time of the captured data associated with the road imperfection and associate this location/time data with the stored vibration data for use in generating graphical representations of road imperfections.

Next, at step 206, the pattern recognition module analyzes the illumination level data (e.g., data captured by the sensing unit's optical camera) present in the retrieved target road condition data to identify potential low illumination sections of road. For example, as a vehicle 110 travels along the road 5 in FIG. 2, the illumination level data will indicate relatively consistent illumination (e.g., either a consistent daylight luminous intensity or, during the night, a consistent artificial light luminous intensity). However, where the vehicle 110 travels on a portion of road where a street light is out—or that is otherwise poorly lit—the illumination level data will deviate significantly and indicate an abnormal illumination level (e.g., a sharp change in illumination intensity). Accordingly, the pattern recognition module is configured to identify deviations or abnormalities in the illumination level data. In addition, the pattern recognition module may be configured to compare the illumination level data in the target data with historical illumination level data to identify changes in illumination levels over a period of time (e.g., by comparing earlier illumination level measurements captured at a particular location at a particular time of day with the most recent illumination level measurement for the particular location at the particular time of day to identify illumination level deviations or abnormalities).

As shown in FIG. 4, if the pattern recognition module does not detect low illumination levels based on the illumination level data, the module moves to step 208. However, if the pattern recognition module does detect low illumination levels, the module moves to step 207 where the associated data is stored (e.g., in the server's memory storage areas). In addition, at step 207, the pattern recognition module will again determine the location and time of the captured data associated with the low illumination levels and associate this location/time data with the stored illumination level data for use in generating graphical representations of road imperfections.

Next, at step 208, the pattern recognition module generates a graphical representation of various road conditions indicated by the target road condition data. For example, in one embodiment, the graphical representation may comprise an interactive road map showing the location of potential road imperfections (e.g., potholes or debris) and low illumination areas (e.g., where a street or tunnel light is out). In this way, a user is able to view road conditions existing within the parameters set for the target data (e.g., hazards within a particular area and/or time period). In addition, the interactive road map may be configured to automatically match before and after images and/or data regarding a particular condition so the user is provided with comparative information about the current and prior state of the condition. For example, in one embodiment, a user may select a particular road hazard on the map and the pattern recognition module will retrieve the most recent image of the hazard (e.g., an image of a pothole captured by the optical camera) and next most recent image of the hazard (e.g., an earlier image of the same location before pot hole was formed).

As will be appreciated from the description herein, various embodiments of the pattern recognition module may be configured to analyze additional road condition data to identify other road conditions. For example, as noted above, the sensing unit 121 may be configured to capture reflectivity data indicative of the reflection coefficient of a road surface. As such, the pattern recognition module may be configured to analyze any captured reflectivity data and identify data indicating an abnormal reflectivity (e.g., where the road is wet or icy). Additionally, the pattern recognition module may be configured to similarly analyze infrared data (e.g., to identify iced roads) and noise data (e.g., to identify debris or road imperfections). Furthermore, the pattern recognition module may be configured to show conditions indicated by this additional data on any generated graphical representations, such as the interactive map noted above. The pattern recognition system may also be configured to identify additional conditions indicated by the road condition data. For example, in certain embodiments, the illumination level data and reflectivity data may be used to indicate weather conditions in a particular area (e.g., sunny, cloudy, raining, etc.). In addition, the condition of painted lines on roads (e.g., lane markers) may be evaluated based on captured video data, reflectivity data, or the like (e.g., to determine whether painted lines are weathered and need to be repainted).

In various embodiments, the pattern recognition module may also be configured to use the hazards or conditions to calculate a road condition index representing a relative hazard level for a particular road or area. For example, in certain embodiments, the road condition index may be calculated using a predetermined function of the number of identified hazards occurring over a given length of road and/or the illumination level over a given length of road. In further embodiments, the predetermined function for calculating the road condition index may take into account the severity of the identified hazards. For example, in various embodiments, a deep pot hole indicated by surface profile data may be weighted more heavily in the road condition index calculation than a light bump indicated by the vibration data. In certain embodiments, the sensor array may also be configured to direct certain optical cameras towards road signs or mile markers and captures images indicating where other associated road condition data is being captured.

Use of Road Condition Sensor Arrays in Vehicle Fleet

According to various embodiments, the road condition detection system 100 may be adapted for use with a fleet of vehicles in order to provide comprehensive road condition updates. The vehicle fleet may be, for example, that of a freight or mail carrier (e.g., the United States Postal Service or United Parcel Service, Inc.), a public transportation provider (e.g., city buses and/or taxis), or one or more rental car agencies. In such embodiments, road condition sensor arrays 120 are provided on numerous vehicles in the fleet and configured to transmit captured road condition data to the central server 170. In this way, road condition data indicative of all roads on which the equipped vehicles travel can be collected and analyzed by the central server 170 (e.g., using the methods described above). By providing road condition sensor arrays on one or more large vehicle fleets, road condition data may be captured and analyzed to indicate road conditions over a wide area.

In embodiments where the central server 170 receives large amounts of road condition data from road condition sensor arrays 120 in a vehicle fleet, the server's pattern recognition module may be configured to repeat steps 202-208 for all received road condition data in order to continuously identify potential road hazards. In various embodiments, information about identified road conditions may be communicated to the Department of Transportation, local media outlets, online road condition services, directly to user devices 180, and/or stored by server 170. In addition, the pattern recognition module may be further configured to continuously update the above-described interactive map (e.g., by periodic updates in accordance with the transmission of road condition data from the onboard computers 130 to the server 170 and by immediate "alert" updates in the scenarios noted above). This updated, global interactive road map may also include calculated road condition indexes.

In various embodiments, the global interactive map may be made accessible via a website or other remote application such that it can be accessed via the network 150 and viewed one a remote personal computer, smart phone, or other device. In this way, the interactive map can be accessed and viewed by drivers, government agencies, and others interested in updates on the status of potential road hazards. In further embodiments, the central server 170 may be configured for indicating potential road hazards on other map-based systems, such as Google Maps, Bing Maps, or Apple Maps. As noted above, the road condition information provided in this way may be used to plan road repairs, salting, other road maintenance, as well as to provide status updates for commuters in order to avoid traffic and potential vehicle damage.

CONCLUSION

As will be appreciated from the description herein, the components and operation of the road condition detection system 100 may be modified according to various embodiments. For example, various sensing devices may be employed in the road condition sensor array's sensing unit 121 to capture a variety of road condition data. In addition, the central server 170 may be configured accordingly to identify various hazards and other conditions based on the captured road condition data using various methods or algorithms. Moreover, according to various embodiments, the road condition data may be processed as described herein by the central server 170, the onboard computer 130, any other suitable computing device, or some combination thereof.

Indeed, many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system for detecting and monitoring road conditions, the system comprising:
   one or more memory storage areas comprising historical illumination data associated with particular locations on one or more road surfaces and associated with particular times of day; and
   one or more processors in communication with the one or more memory storage areas;
   wherein the one or more processors are, collectively, configured to:
   monitor road condition data captured by one or more road condition detection systems provided on a vehicle, the one or more road condition detection systems comprising:
   a vibration sensor configured to capture vibration data indicative of the magnitude and frequency of vibration of the vehicle;
   an optical camera comprising an aperture configured to receive light from the one or more road surfaces traveled by the vehicle;
   an optical sensor configured to capture illumination data associated with an intensity of the light received through the aperture;
   a location determining device configured to determine the location of the vehicle on the one or more road surfaces; and
   a real-time clock configured to indicate a time of day;
   capture, for storage in the one or more memory storage areas, road condition data from the one or more road condition detection systems, wherein the captured road condition data is indicative of one or more road condition attributes of the one or more road surfaces traveled by the vehicle, the road condition data comprising:
   vibration data from the vibration sensor; and
   illumination data from the optical sensor;
   associate location data from the location determining device and time of day data from the real-time clock with the road condition data captured by the vibration sensor and the optical sensor;
   retrieve the historical illumination data from the one or more memory storage areas;
   compare the captured illumination data with the historical illumination data corresponding to the locations and the times of day of the captured illumination data;
   identify one or more deviations between the captured illumination data and the historical illumination data;
   store data indicative of the identified one or more deviations between the captured illumination data and the historical illumination data and their respective locations in the one or more memory storage areas;
   identify a change in magnitude or frequency of the captured vibration data that is indicative of one or more potholes existing along the one or more road surfaces;
   determine, based on the captured vibration data, a severity of the identified one or more potholes;
   determine, based on the captured vibration data, the location of the identified one or more potholes;
   store data indicative of the identified one or more potholes and their respective locations in the one or more memory storage areas; and
   determine, based at least in part on the determined severity of the identified one or more potholes, the determined location of the identified one or more potholes, and deviations between the captured illumination data and the historical illumination data, a road condition index value for a road surface, wherein the road condition index value is indicative of the quantity of the identified one or more road potholes along the road surface, the severity of each of the identified one or more potholes along the road surface, and the illumination level along the road surface.

2. The system of claim 1, wherein the one or more processors are configured to determine the location of the identified one or more potholes by temporally associating the location data with road condition attributes indicated in the captured road condition data.

3. The system of claim 1, wherein the captured road condition data comprises reflectivity data indicative of light reflectivity levels along the one or more road surfaces.

4. The system of claim 1, wherein the captured road condition data comprises video data comprising a video recording of the one or more road surfaces; and wherein the one or more processors each are configured to identify deviations in the continuity of the video recording indicative of one or more potholes along the one or more road surfaces.

5. The system of claim 1, wherein the one or more processors are further configured to generate a geographical map display indicating the location of one or more of the identified one or more potholes.

6. The system of claim 1, wherein the one or more processors are further configured to transmit the data indicative of the identified one or more potholes to one or more remote user devices; and wherein the one or more processors are further configured to generate an alert to be transmitted to the one or more remote user devices upon identifying one or more potholes.

7. The system of claim 1, wherein the optical camera is configured for capturing road condition data comprising one or more of:

reflectivity data indicative of light reflectivity levels along the one or more road surfaces; and video data comprising a video recording of the one or more road surfaces.

8. The system of claim 1, wherein the one or more road condition detection systems further comprise a road surface scanner configured for capturing surface profile data indicative of the surface profile of the one or more road surfaces.

9. The system of claim 1, wherein the one or more road condition detection systems comprise a front sensing unit configured for being mounted to a front portion of the vehicle and a rear sensing unit configured for being mounted to a rear portion of the vehicle aft of the front sensing unit.

10. The system of claim 9, wherein one or more sensing devices of the rear sensing unit are configured to capture road condition data corresponding to the road condition data captured by the front sensing unit to confirm the accuracy of the road condition data captured by the front sensing unit.

11. The system of claim 1, wherein the the one or more processors are configured for transmitting the captured road condition data to a remote server.

12. The system of claim 1, wherein the one or more processors are further configured to identify a change in magnitude or frequency of the vibration data that is indicative of a protrusion from the road surface.

* * * * *